United States Patent [19]

Neuwirth et al.

[11] Patent Number: 4,949,718
[45] Date of Patent: Aug. 21, 1990

[54] INTRAUTERINE CAUTERIZING APPARATUS

[75] Inventors: Robert S. Neuwirth, Englewood, N.J.; Lee R. Bolduc, Raleigh, N.C.

[73] Assignee: Gynelab Products, Raleigh, N.C.

[21] Appl. No.: 242,730

[22] Filed: Sep. 9, 1988

[51] Int. Cl.⁵ .................................................. A61F 7/12
[52] U.S. Cl. ...................................... 128/401; 606/27
[58] Field of Search ............... 128/6, 303.1–303.12, 128/399–402; 600/18; 604/99; 606/27, 28

[56] References Cited

U.S. PATENT DOCUMENTS

| | | | |
|---|---|---|---|
| 2,043,083 | 6/1936 | Wappler | 128/303.11 |
| 2,074,634 | 3/1937 | Ackerman | 128/303.12 |
| 2,077,453 | 4/1937 | Albright | 128/254 |
| 2,078,786 | 4/1937 | Wood | 128/303.12 |
| 2,190,384 | 2/1940 | Newmen | 128/400 |
| 2,192,768 | 3/1940 | Cross | 128/401 |
| 2,466,042 | 4/1949 | Reich et al. | 128/401 |
| 2,734,508 | 2/1956 | Kozinski | 128/401 |
| 2,777,442 | 1/1975 | Hart | 128/303.12 |
| 3,369,549 | 2/1968 | Armao | 128/303.1 |
| 3,417,746 | 12/1968 | Moore et al. | 128/6 |
| 3,924,628 | 12/1975 | Droegemueller et al. | 128/303.1 |
| 4,546,759 | 10/1985 | Solar | 600/18 |
| 4,686,965 | 8/1987 | Bonnet et al. | 128/4 |
| 4,754,752 | 7/1988 | Ginsburg et al. | 128/401 |
| 4,793,351 | 12/1988 | Landman et al. | 604/99 |
| 4,834,091 | 5/1989 | Ott | 128/303.1 |

FOREIGN PATENT DOCUMENTS

| | | | |
|---|---|---|---|
| 895046 | 12/1953 | Fed. Rep. of Germany | 128/401 |
| 0728858 | 5/1980 | U.S.S.R. | 128/400 |

Primary Examiner—Max Hindenburg
Attorney, Agent, or Firm—Kenyon & Kenyon

[57] ABSTRACT

A method and apparatus for effecting necrosis of a tissue lining of a mammalian body cavity, particularly a uterine endometrium, by introducing an applicator comprising a distendable bladder connected to a catheter into the uterus, distending the bladder by introducing a non-toxic fluid under pressure, heating the fluid by means located internal to the bladder to a temperature of 190° to 215° F. and preferably 210° F. for a period of 4 to 12 minutes and preferably 6 minutes and regulating said apparatus by means located external to the uterus, thereby cauterizing substantially the entirety of the tissue lining, particularly the endometrium.

20 Claims, 5 Drawing Sheets

INTRAUTERINE CAUTERIZING APPARATUS

BACKGROUND OF THE INVENTION

1. Field of the Invention

This invention relates to an apparatus and a method for cauterizing the tissue lining of a human body cavity, particularly the endometrium of the uterus. More specifically, the apparatus and method of the present invention ensures effective cauterization of the endometrium of a mammalian uterus without many of the disadvantages and dangerous features of known intrauterine cauterization techniques.

2. The Prior Art

The following terms as used herein have the meaning given below:

"Necrosis" means the death of cells in tissue.

"Endometrium" is that portion of the inner lining of the uterus to which an embryo normally attaches and excludes the portions of the uterine inner lining forming the cervix, to which the embryo usually does not attach.

Apparatus and methods for cauterization of the endometrium of a mammalian uterus, useful in sterilization procedures and cancer treatments, are well known. Thermal and cryogenic treatments have been utilized in such cauterization techniques and typically involve either the direct or indirect application of heat or cold to the tissue to be treated.

For example, a laser hysteroscope has been used to cauterize the endometrial layer of the uterus. This laser treatment suffers from several disadvantages. It requires the application of an intense amount of thermal energy to a relatively small area of tissue even though such a large amount of heat may not be necessary to effectively cauterize the tissue. Further, this laser treatment requires the physician to continually re-position the laser used in the treatment within the uterus in order to treat the entire endometrium. Such internal manipulation of a laser hysteroscope within the uterus of a patient is both difficult, requiring a significant level of skill to perform, and potentially dangerous. Accidental puncture of the uterine or tissue wall may result from manipulation of the laser scope within the uterus or body cavity, and tissue layers beneath the endometrium may be burned if a laser's beam is left focused on one area of tissue for too long a period of time.

A variety of alternatives to laser treatment in cauterizing the uterine endometrium are known. In U.S. Pat. No. 3,924,628, Droegemueller et al. disclose a method and apparatus for necrosing tissue cells that utilizes an extendable bladder which is inserted in the uterus and filled with a circulating fluid or gas at cryogenic temperatures (referring to temperatures sufficiently low to cause cell necrosis). The bladder disclosed by Droegemueller et al. is maintained in substantially continuous contact with the inner surface of the uterine lining and achieves necrosis of substantially all of the uterine endometrium in a single treatment. Droegemueller et al. disclose the use of liquid nitrogen that vaporizes prior to introduction into the bladder, thereby pressurizing the bladder to a level which ensures adequate contact with the uterus. Other fluids disclosed by Droegemueller et al. as useful in their method include refrigerants such as freon. Droegemueller et al.'s method and apparatus suffers from the disadvantage of employing cryogenic fluids which could prove toxic to a patient in the event of bladder rupture. Moreover, Droegemueller et al.'s apparatus does not allow regulating the pressure used to inflate the bladder. Another disadvantage of Droegemueller et al.'s technique is that cryogenic necrosis of the endometrium occurs at extremely low temperatures that pose a threat to tissue layers adjacent to the uterine endometrium. Droegemueller et al. and similar cryogenic techniques also require the use of expensive equipment such as compressors and insulated vessels associated with the storage and transmission of refrigerants. Moreover, Droegemueller et al.'s technique may require warming of the bladder in order to remove it from the body and minimize tearing of the surrounding tissue which has adhered to the bladder during the freezing process.

In U.S. Pat. No. 2,734,508, Kozinski discloses a therapeutic apparatus for applying dry heat to body cavities comprising an applicator that is introduced in the body cavity while deflated and which is subsequently inflated and heated by means of circulating hot air. Kozinski does not disclose an applicator which conforms to the shape of a body cavity. Further, given the lower heat transfer coefficients of gases as compared with liquid, treatment with Kozinski's apparatus should involve a long period of time in order to achieve necrosis, thereby exposing the patient to additional discomfort and risk. Moreover, Kozinski's apparatus does not provide for measurement and regulation of internal pressures and temperatures of the applicator introduced.

U.S. Pat. No. 2,077,453, issued to Albright, discloses a therapeutic appliance comprising a relatively long tubular applicator which is shaped and formed generally to the passage into which it is to be inserted and which has relatively thin elastic rubber walls that transfer heat and which distend to fit irregularities of the treated areas upon application of internal pressure. Albright also discloses that fluids such as heated water could be utilized as a heating means in his applicator. The applicator of Albright, like that of Kozinski, however, suffers from the disadvantage that the distension of its walls to conform to the irregularities of the endometrium is limited as Albright provides an integral rubber web which serves to prevent undue distension of the applicator. Moreover, Albright requires that the fluid be circulated throughout the apparatus. Albright also does not provide an apparatus that allows regulation of temperature and pressure of the fluid or other bladder inflation means.

U.S. Pat. No. 3,369,549, issued to Armao, discloses a therapeutic device for applying heat or cold to body cavities comprising a capsule probe containing a heat exchanger and a flexible bladder that can be inflated to conform to a body cavity. Armao does not, however, disclose a control means for regulating the temperature and pressure of the flexible applicator, nor does he disclose cauterizing tissue in the cavity being treated.

Other patents that disclose the use of thermal treatment of the interior lining of a body cavity include U.S. Pat. Nos. 2,192,768; 2,466,042; 2,777,445; and 3,369,549.

SUMMARY AND OBJECTS OF THE INVENTION

It is an object of the present invention to provide a safe and efficacious method for cauterizing the tissue lining of a body cavity, particularly the endometrium of a uterus.

It is another object of the present invention to provide a relatively inexpensive and easy to replace applicator heated by a nontoxic fluid that can be used to effect cauterization of the uterine endometrium and which is controlled by means external to the applicator.

It is another object of the present invention to provide a non-fluid circulating apparatus for heating a fluid while it is in a bladder within the uterus and for introducing the fluid under pressure into the bladder so as to assure substantially uniform contact of the bladder with the endometrium.

It is still another object of the present invention to provide an apparatus for regulating the temperature and pressure of the fluid in the bladder while the bladder is within the uterus.

The present invention provides a method for effecting cauterization necrosis of the tissue lining of a mammalian body cavity comprising the steps of inserting a distendable bladder into the body cavity; inflating said distendable bladder to a predetermined pressure with a fluid so that said distendable bladder is in contact with substantially all of the tissue lining for which necrosis is desired; heating said fluid by means of a heating element positioned internal to said distendable bladder; controlling the temperature and pressure of said fluid by control means connected to said distendable bladder; and maintaining said bladder so inflated with said fluid at a temperature for a period of time sufficient to effect cauterization necrosis of substantially all of the tissue lining of the body cavity for which necrosis is desired.

The present invention also provides a method for effecting cauterization necrosis of an uterine endometrium comprising the steps of inserting a distendable bladder into the uterus; inflating said distendable bladder to a predetermined pressure with a fluid so that said distendable bladder is in contact with substantially all of the endometrium; heating said fluid by means of a heating element positioned internal to said distendable bladder; regulating the temperature and pressure of said fluid by control means connected to said distendable bladder; and maintaining said bladder so inflated with said fluid at a temperature for a period of time sufficient to effect cauterization necrosis of substantially all of the uterine endometrium.

The present invention further provides a method for cauterizing substantially the entirety of the endometrium of a mammalian uterus by application within an inflatable bladder of a fluid at a pressure of 40 to 140 mmHg and preferably about 75 mmHg, heated to a temperature of 140° to 215° F. and preferably about 210° F. for a period of 4 to 12 minutes, with a preference of around 6 minutes, thereby realizing substantial necrosis of substantially all of the uterine endometrium without significant damage to surrounding tissue.

The present invention also provides an apparatus for effecting necrosis of the tissue lining of a body cavity, and, in particular, substantially the entirety of the endometrium of a mammalian uterus comprising an applicator which comprises a catheter for insertion into the uterus, said catheter having a proximal end and a distal end, and a distendable bladder attached to said proximal end; inflating means connected to said distal end for distending said distendable bladder; heating means positioned internal to said distendable bladder for heating said distendable bladder; and control means for regulating the distending and heating of said distendable bladder.

The present invention provides an apparatus for effecting cauterization necrosis of the tissue lining of a body cavity, and, in particular, substantially the entirety of the endometrium of a mammalian uterine comprising means for contacting the endometrium with an applicator comprising an inflatable bladder mounted on a length of rigid tubing attached to a length of flexible tubing; means for positioning the bladder in the uterus; means for distending the inflatable bladder, so as to assure substantially uniform contact with the endometrium, by introduction of a fluid under pressure into the applicator from a fluid source positioned external to the uterus; means for heating the bladder, comprising heating the fluid by a heating element positioned internal to the bladder; control means positioned external to the uterus and connected to the applicator by the flexible tubing and at least one wire connected to the heating element for regulating the distending and heating of the bladder; and means for disengaging the applicator from the control means so as to separate the applicator from the control means.

These and other objects of the present invention are achieved by a method in which necrosis of the endometrium of a mammalian uterus may be achieved by insertion of an applicator comprising rigid and flexible tubing and a readily distendable high strength bladder material into the uterus; introduction of a fluid through the tubing into the distendable bladder at a pressure of 40 to 140 mmHg and preferably about 75 mmHg, thereby inflating the bladder so that it substantially conforms to the irregularities in the shape of the endometrium; the pressure of the fluid measured and regulated by means external to the uterus; heating the fluid to a temperature of 140° to 215° F. and preferably about 210° F., for a period of 4 to 12 minutes, with a preference of around 6 minutes, by heating means positioned within the distendable bladder and regulated by control means external to the applicator, thereby cauterizing substantially the entirety of the uterine endometrium.

DESCRIPTION OF A PREFERRED EMBODIMENT

Figure 1:
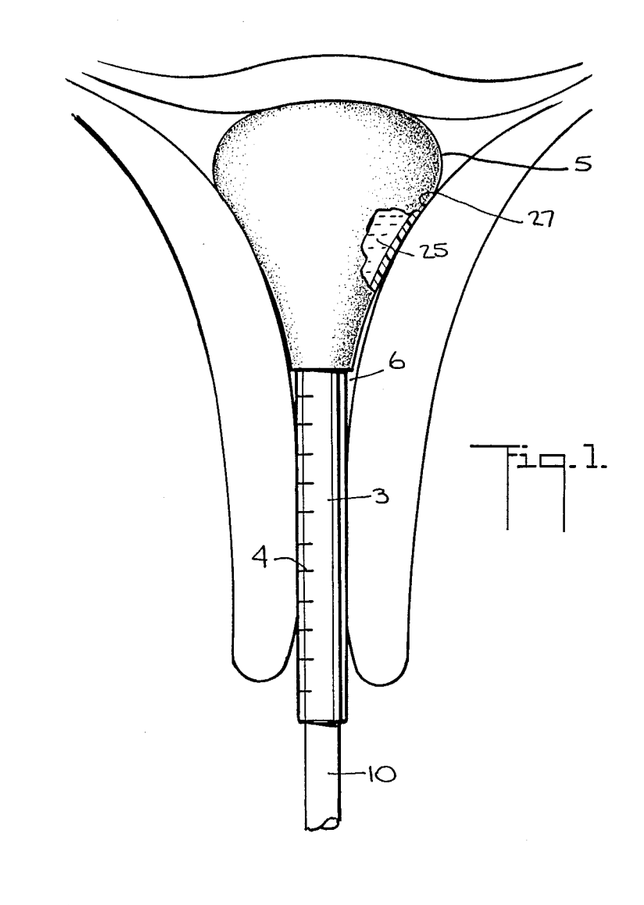
FIG. 1 depicts a distendable bladder utilized in the method of the present invention which has been inserted into and inflated within a mammalian uterus.

FIG. 1 shows an inflated distendable bladder 5 attached to rigid tubing 3 located within a human uterus 6. Inflation of the distendable bladder 5 with a fluid 25 assures uniform contact of the bladder with the endometrial tissue layer 27 of mammalian uterus 6.

The rigid tubing 3 and the attached distendable bladder 5 must be sufficiently small, when the distendable bladder is deflated, so that it can be conveniently and safely inserted into the uterus 6 through a partially dilated cervix 22. The rigid tubing with the deflated bladder is aligned with the cervical canal after the cervix is exposed with a speculum and grasped with a tenaculum. After the distendable bladder 5 has been inserted, the distendable bladder 5 should be inflated to a pressure sufficient to ensure firm contact with the tissue to be necrosed, in this case the endometrial tissue layer on the interior uterine surface, but should preferably be maintained at or about 40 to 140 mmHg, and preferably about 75 mmHg, to minimize risk of rupture of the distendable bladder 5 and possible internal injury to the patient.

Distendable bladder 5 must be capable of withstanding high temperatures without rupturing, and preferably have as good a heat transfer characteristic as is obtainable in such materials to provide efficient heating action. A distendable bladder of a heat curing rubber such as latex has been found satisfactory.

Fluid 25 preferably should be a sterile non-toxic fluid with a boiling point of at least 212° F. A five percent dextrose in water solution has been found satisfactory.

Figure 2:
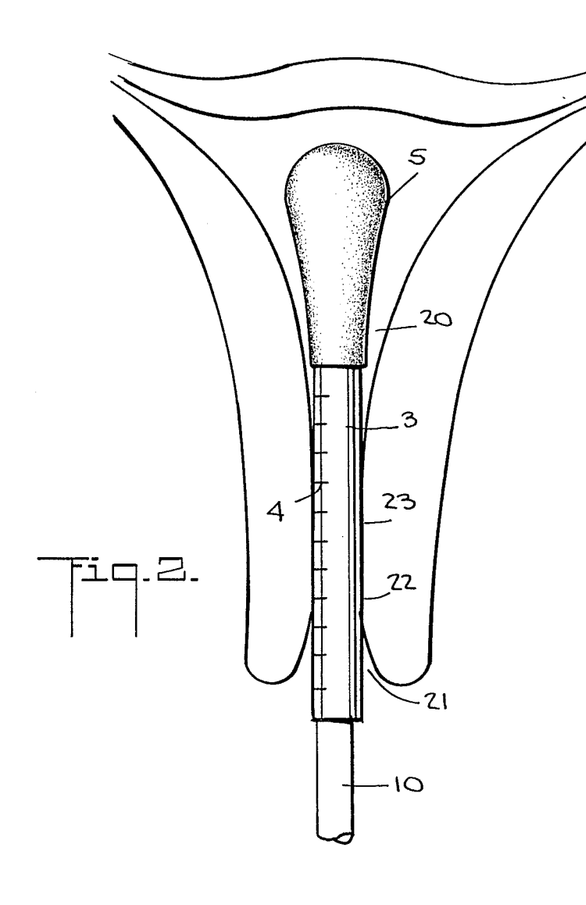
FIG. 2 depicts placement of the distendable bladder within a mammalian uterus.

As illustrated in FIG. 2, the uninflated distendable bladder 5 attached to rigid tubing 3 is inserted into the vagina 21, past the cervical os 22, through the cervical canal 23, for placement in the uterine cavity 20. Placement may be aided by virtue of scale gradations 4 located on the rigid tubing 3 to indicate the depth of insertion of the bladder 5. Rigid tubing 3 is attached to a control unit 30 (shown in FIG. 3) via flexible tubing 10.

Figure 3:
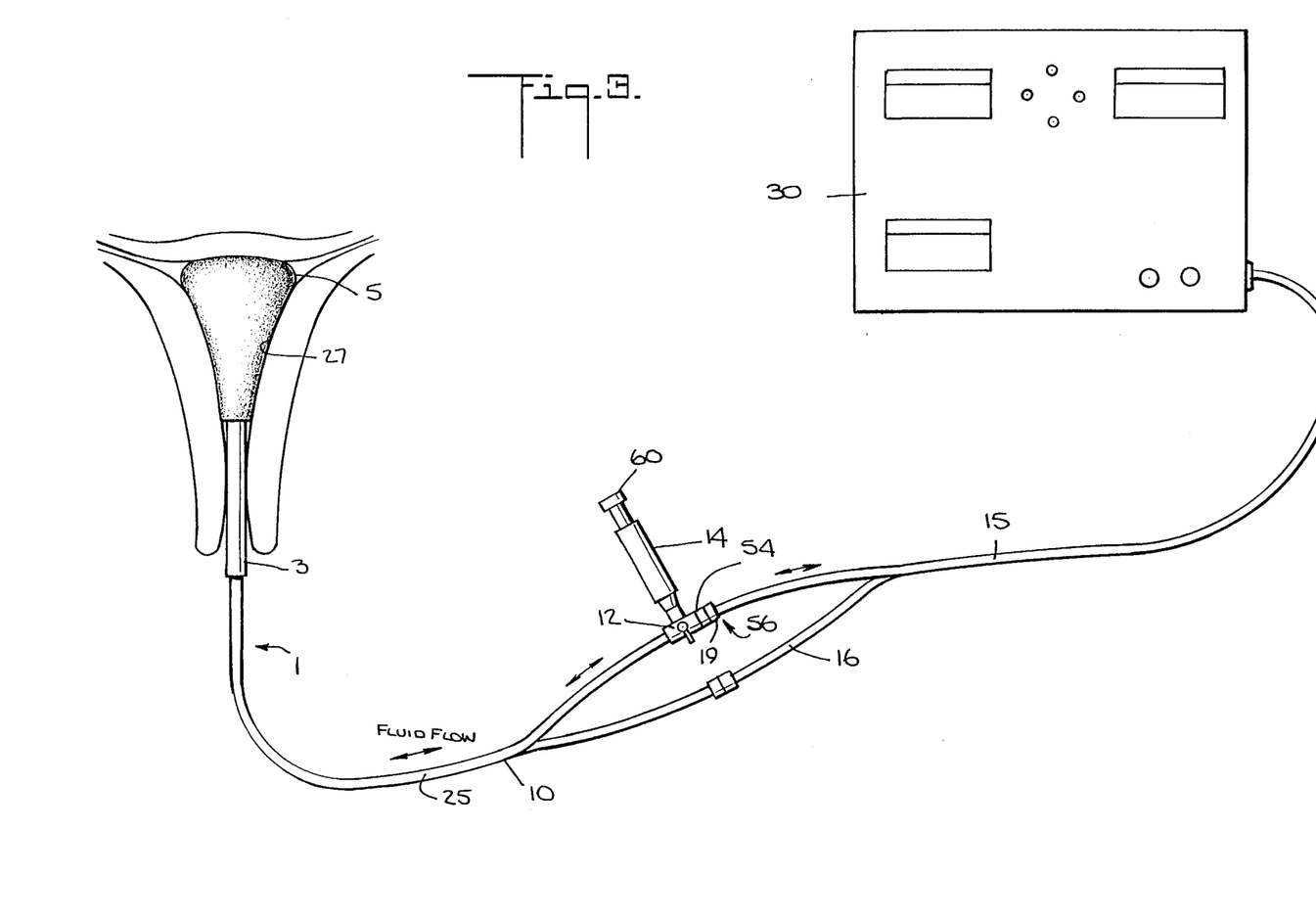
FIG. 3 is a view of an apparatus constructed in accordance with the invention that illustrates the applicator connections.

FIG. 3 depicts the arrangement of control unit 30 and applicator end 1, comprising the distendable bladder 5, rigid tubing 3 and flexible tubing 10, and the interconnection of those elements. A fluid system 55 comprises that portion of the invention through which the fluid 25 travels, including a hypodermic barrel 14 or other fluid source (not shown), flexible tubing 10, rigid tubing 3, distendable bladder 5 and control unit 30. Manipulation of the hypodermic barrel 14 enables the operator of the system to control the amount of fluid 25 in the fluid system 55, inflation and deflation of the distendable bladder by adding or removing fluid, respectively, and pressure of the fluid 25 in the system. Hypodermic barrel 14 also provides protection for the patient by allowing fast and safe reduction of excessive pressures in the system that might build up through some malfunction.

Manipulation of the hypodermic barrel 14 by depressing a plunger 60 causes fluid 25 to be introduced through 3-way stopcock 12 into the flexible tubing 10, and to the rigid tubing 3. The fluid 25 emerges from rigid tubing 3 and into distendable bladder 5, forcing distendable bladder 5 to expand into contact with the endometrial tissue layer 27 of the uterus 6. The fluid 25 is also directed along the flexible tubing to the control unit 30 allowing measurement of the fluid pressure within the bladder by well known means.

Each of the parts of the fluid system 55 is in fluid communication providing constant fluid pressure within the entire fluid system 55 and allowing measurement of the pressure at the applicator end 1 via measurement of pressure of the end attached to the control unit 30.

Control unit 30 is connected to applicator end 1 via plastic sheath 15 which contains flexible tubing 10 and electrical sheath 16. Flexible tubing 10 is connected to a fluid joint 56 via pressure transducer 54, by well known means. Using a standard luer lock connector 19, pressure transducer 54 and hypodermic barrel 14 are connected to flexible tubing 10 via a readily available 3-way stopcock 12. 3-way stopcock 12 may be used to isolate the hypodermic barrel 14 or other fluid source from the fluid system 55 once the desired fluid pressure is reached.

Figure 4:
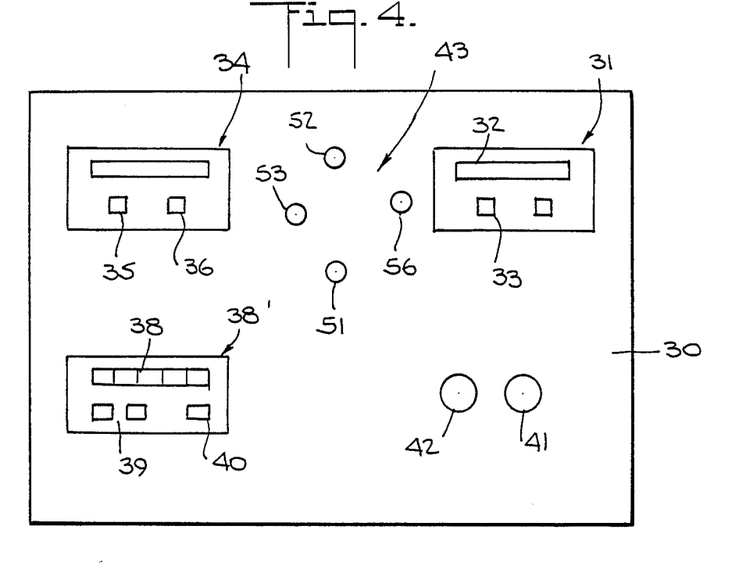
FIG. 4 depicts a system control unit.

FIG. 4 depicts control unit 30, consisting of fluid temperature control 31, fluid pressure control 34, time control 38' and a power source (not shown). The control unit 30 includes a power switch 42 and fuse 41. Fluid temperature is regulated by fluid temperature control 31 and is set by temperature set/reset button 33. The temperature of fluid 25 in the distendable applicator 5 is shown at temperature display 32.

Fluid pressure within the fluid system 55 is regulated by means of controls located on fluid pressure control panel 34. The upper limit for fluid pressure is controlled by high pressure set/reset button 35, with the lower limit controlled by low pressure set/reset button 36. Fluid pressure in mmHg is shown by LED pressure display 37. Control unit 30 also has pressure indicator display 43, which upon introduction of fluid 25 into the fluid system 55 provides an easy to see visual display of fluid pressure within the fluid system 55.

Time for the procedure is shown at time display 38, which displays both lapsed time and time remaining for the procedure. Total time for the procedure may be easily set in minutes, seconds, and tenths of seconds using time set buttons 39 and may be cleared or reset using time clear/reset button 40.

Figure 5:
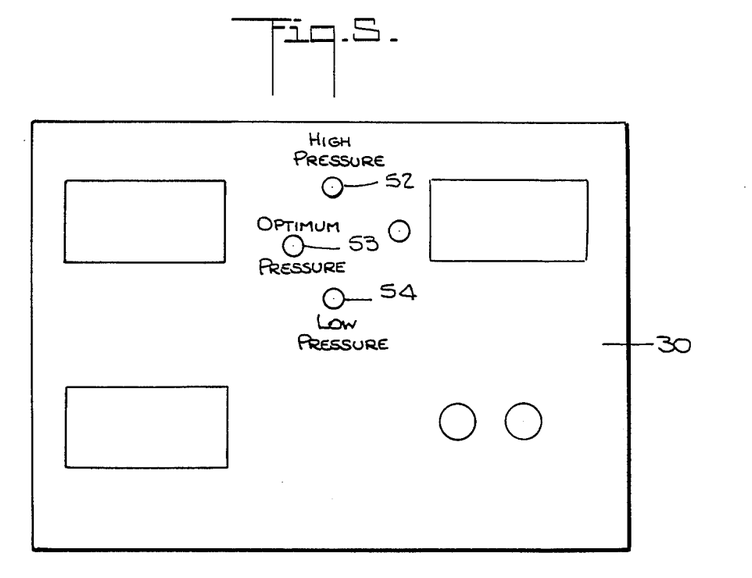
FIG. 5 is a detail view of a pressure limiting and safety monitor.

A simplified means for determining whether the fluid 25 is within the preset pressure range is depicted in FIG. 5, which illustrates the pressure indicator display 43. The pressure indicator display 43 is comprised of a low pressure indicator 51, a high pressure indicator 52 and an optimum pressure indicator 53. As fluid 25 is introduced into the fluid system 55 by manipulation of hypodermic barrel 13, the pressure indicator display 43 is successively illuminated as various fluid pressures are reached. Low pressure indicator 51 is illuminated when fluid pressure is below the preset range. High pressure indicator 52 is illuminated when fluid pressure is above the preset range. Optimum pressure indicator 53 is illuminated when fluid pressure is within the preset range.

These indicators allow the practitioner to readily reach the preset pressure range by varying the amount of fluid in the fluid system via manipulation of the hypodermic barrel 14. A separate heating element indicator 55 is also provided to indicate when power is being provided to a heating element 44 located within the distendable applicator 5.

Figure 6A:
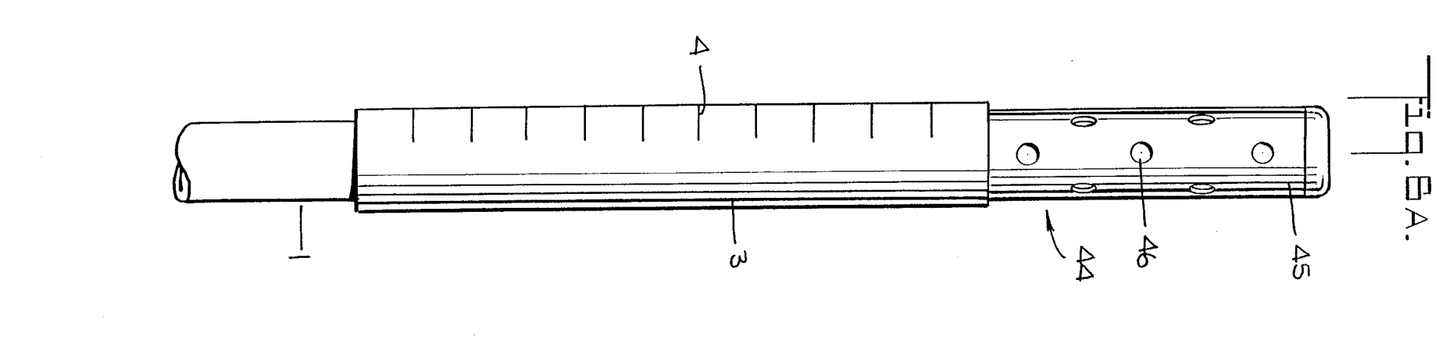
FIG. 6A is the vented heating element shield utilized in the method of the present invention.
Figure 6B:
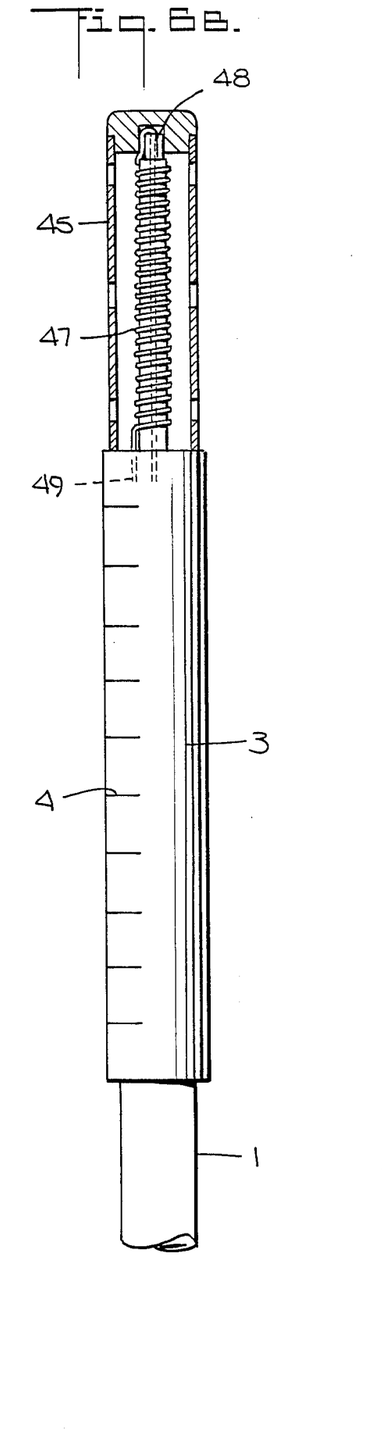
FIG. 6B is a cutaway view of the vented heating element shield showing the heating element and thermocouple.

Two views of heating element 44 are shown in FIGS. 6A and 6B. FIG. 6A is an external view of heating element 44, which comprises heating element coil shield 45 and ventilation holes 46.

FIG. 6B is a cutaway view of heating element 44, wherein wire leads 49 provide power from system control unit 30 to heating element coil 47 causing heating element coil 47 to heat the fluid 25 which comes into contact with the heating element coil 47 as the fluid 25 flows through the ventilation holes 46. Temperature of the fluid 25 is measured by thermocouple 48 and is displayed at temperature display 32. Heat element coil shield 45 prevents distendable bladder 5 from contacting the heating element coil 47.

Figure 7:
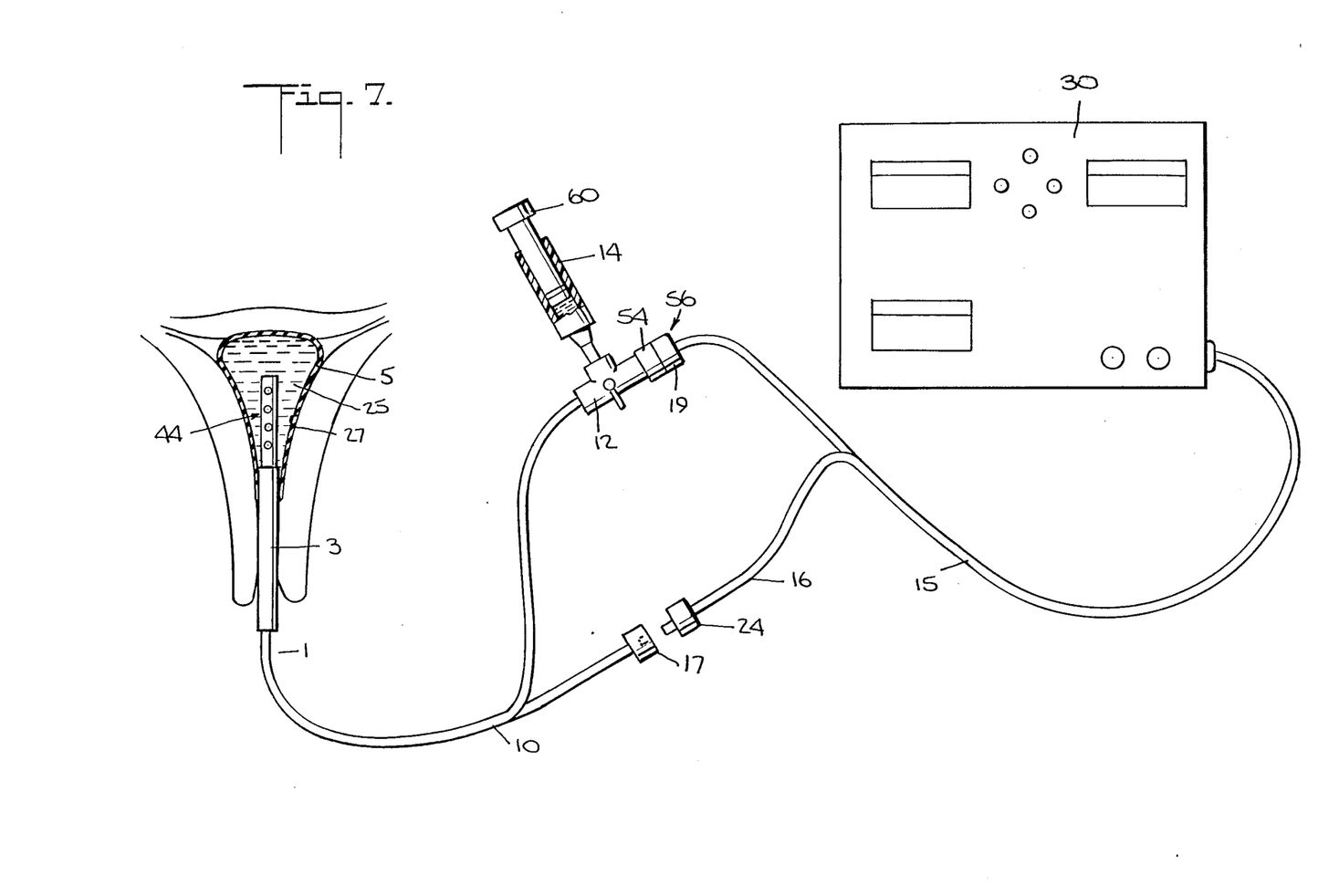
FIG. 7 depicts a means for connecting and disconnecting the applicator.

The applicator end 1 is designed to be easy to replace as shown in FIG. 7, which depicts control unit end 30' and applicator end 1 of the invention. Control unit end 30' is composed of electrical sheath 16 which is attached on one end to control unit 30 and on the other end to male electrical connector 24, which allows transmittal of power to the heating element 44. Male electrical connector 24 is readily attached or disattached to female electrical connector 17 on the applicator end 1.

Control unit end 30' is also comprised of components from the fluid system 55, including flexible tubing 10 attached to 3-way stopcock 12. 3-way stopcock 12 provides control over the introduction and removal of fluid 25 via hypodermic barrel 14. The applicator end 1 is easily connected or disconnected from the 3-way stopcock via a luer lock connector 19 attached to pressure transducer 54.

The invention will now be illustrated by the following example.

EXAMPLE

The cauterization procedure is preceded by screening against cancer of the affected region and physical condition within established norms. A PAP smear and endometrial biopsy/curettage must exclude cancer or precancerous lesions of the uterus and cervix. If a fibroid uterus is present, an ultrasound should exclude ovarian masses. The uterine cavity must be 10 cm or less in length to be suitable for the small distendable bladder size.

The patient should be post menstrual or start on Danazol, or the equivalent which causes reduction in bleeding and a thin endometrium, at a rate of 800 ml daily, from the 5th day of the previous menstrual period until two weeks after the procedure. She will undergo the procedure in the ambulatory surgery unit or outpatient facility where Valium and/or Demerol can be given intravenously if there is pain during the heating phase of the procedure.

The applicator will be inserted after a bimanual examination and speculum of the cervix. Dilation to 6 mm. may be required which may necessitate a local 1% lidocane block of the cervix. Once in place the applicator stem protrudes from the vagina and consists of an electrical connecting plug and rigid tubing. Placement of the applicator may be facilitated by distance markings on the rigid tubing indicating depth of insertion.

Upon placement of the applicator it will be connected to a control unit via attachment of the electrical connector and flexible tubing attached to the rigid tubing to their counterparts extending from the control unit.

Subsequent to insertion of the applicator, the control unit will be powered on in order to allow the practitioner to set the system constraints. The temperature of the fluid in the bladder will be set at the temperature control panel and can be measured via the thermocouple located within the bladder. Fluid pressure constraints are set at the pressure control panel, and upon inflation of the distendable bladder by introduction of fluid to the fluid system by depressing the plunger on the hypodermic barrel, can be easily measured by looking at the pressure indicator lights located on the control unit.

The practitioner then proceeds to inflate the distendable bladder by rotating the lever on the 3-way stopcock in order to access the fluid source and depressing the plunger on the hypodermic barrel which may serve as the fluid source. The practitioner injects the fluid into the fluid system until the pressure indicator lights indicate that the fluid pressure is within the pre-set constraints. At that point, the practitioner manipulates the 3-way stopcock to close off access to the fluid system by the fluid remaining in the hypodermic barrel. Thus, the fluid is non-circulating during the heating portion of the procedure, in part allowing more precise measurement of fluid temperature. The volume of fluid necessary to inflate the bladder will vary from 3 to 20 ml in most cases in order to reach the pressure wherein the bladder is substantially in contact with all of the endometrium.

The practitioner then turns on the heating element in order to heat the fluid to a pre-set level. The heating element in the bladder is connected via the plug to a 12 volt system which will bring the fluid in the bladder to the level of boiling as needed for each particular local, i.e. 190 degrees farenheit in Mexico City, and 212 degrees farenheit in New York City. Once that temperature level is reached, the system timer is activated to time the procedure and provide automatic turn off of the heating element at the end of a preset period.

Upon completion of the procedure, the 3-way stopcock is again manipulated to allow the fluid to be withdrawn from the fluid system causing the distendable bladder to deflate. Upon deflation of the distendable bladder, the applicator may be safely withdrawn from the patient. The coagulated endometrium is then removed from the endometrial cavity with a curette, leaving the underlying surface free to form adhesions with the other opposing surfaces of the endometrial cavity.

What is claimed is:

1. An apparatus for effecting necrosis of an uterine endometrium comprising:
    a catheter having a proximal end and a distal end;
    a distendable bladder means attached to said proximal end for insertion into and distending the uterus;
    inflating means connected to said distal end for introducing an inflation medium into said bladder;
    heating means for heating said inflation medium to a temperature sufficient to effect tissue necrosis positioned internal to said bladder; and
    control means connected to said distal end for regulating the inflating and heating of said bladder.

2. The apparatus of claim 1, wherein said catheter is comprised of rigid tubing at the proximal end of said bladder, and flexible tubing extending through said rigid tubing from said control means to said bladder.

3. The apparatus of claim 2, wherein said inflating means comprises a pump means connected to said flexible tubing for pumping said inflation medium through said flexible tubing so as to inflate said bladder.

4. The apparatus of claim 3, wherein said pumping means comprises a hypodermic barrel.

5. The apparatus of claim 4, wherein said hypodermic barrel is connected to said flexible tubing by a three-way valve.

6. The apparatus of claim 3, wherein said fluid is non-circulating.

7. The apparatus of claim 2, wherein said rigid tubing is selected from the group comprising Teflon type tubing.

8. The apparatus of claim 2, wherein said flexible tubing is selected from the group comprising Teflon type tubing.

9. The apparatus of claim 2, further comprising a positioning means for positioning said distendable bladder in the uterus.

10. The apparatus of claim 9, wherein said positioning means comprises scale gradations on said catheter for indicating depth of insertion of said distendable bladder into the uterus.

11. The apparatus of claim 1, further comprising means for disengaging said catheter from said control means so that the applicator and the control means may be separated.

12. The apparatus of claim 1, wherein said distendable bladder is capable of resisting an internal pressure of at least 300 mmHg without rupturing and a temperature of at least 250° Fahrenheit without carbonizing.

13. The apparatus of claim 12, wherein said bladder is selected from the group comprising latex rubber.

14. The apparatus of claim 1, wherein said control means comprises:
volume control means;
temperature control means
pressure control means; and
time control means.

15. The apparatus of claim 14, wherein said temperature control means comprises a thermocouple for measuring the temperature of said inflation medium fixed to the proximal end of said catheter and positioned internal to said bladder; said thermocouple connected to said control means via a second electrical lead.

16. The apparatus of claim 14, wherein said pressure control means comprises;
a pressure sensor connected to said flexible tubing;
said pressure sensor connected to a pressure display means for displaying and regulating the pressure of said inflating means.

17. The apparatus of claim 14, wherein said time control means comprises a clock.

18. The apparatus of claim 17, wherein said clock is programmable and connected to said temperature control means.

19. An apparatus for effecting necrosis of a tissue lining in a body cavity comprising:
a catheter comprising a length of flexible tubing having a distal end and a proximal end;
a bladder means for insertion into and distending the body cavity attached to a proximal end;
inflating means connected to said distal end for introducing an inflation medium through said flexible tubing and into said bladder;
a heating means for heating said inflation medium to a temperature sufficient to effect tissue necrosis positioned internal to said bladder; and
control means connected to said distal end for regulating inflation and heating of said bladder.

20. The apparatus of claim 19 further comprising a thermocouple for measuring the temperature of said inflation medium positioned internal to said bladder and connected to said control means via an electrical lead.

* * * * *

UNITED STATES PATENT AND TRADEMARK OFFICE

CERTIFICATE EXTENDING PATENT TERM
UNDER 35 U.S.C. § 156

| | | |
|---|---|---|
| PATENT NO. | : | 4,949,718 |
| ISSUED | : | August 21, 1990 |
| INVENTORS | : | Robert S. Neuwirth, et al. |
| PATENT OWNER | : | Gynelab Products |
| PRODUCT | : | ThermaChoice™ Uterine Balloon Therapy System |

This is to certify that an application under 35 U.S.C. § 156 has been filed in the U.S. Patent and Trademark Office, requesting extension of the term of U.S. Patent No. 4,949,718 based upon the regulatory review of the product ThermaChoice™ Uterine Balloon Therapy System by the Food and Drug Administration. Since it appears that the requirements of the law have been met, this certificate extends the term of the patent for the period of 605 days from September 9, 2008, the original expiration date of the patent, subject to the provisions of 35 U.S.C. § 41(b), with all rights pertaining thereto as provided by 35 U.S.C. § 156(b).

I have caused the seal of the U.S. Patent and Trademark Office to be affixed this 12th day of September 2000.

Q. Todd Dickinson
Under Secretary of Commerce for Intellectual Property
and Director of the United States Patent and
Trademark Office

US004949718B1

REEXAMINATION CERTIFICATE (3668th)
United States Patent [19]
Neuwirth et al.

[11] B1 4,949,718
[45] Certificate Issued Nov. 10, 1998

[54] INTRAUTERINE CAUTERIZING APPARATUS

[75] Inventors: Robert S. Neuwirth, Englewood, N.J.; Lee R. Bolduc, Raleigh, N.C.

[73] Assignee: Gynelab Products, Raleigh, N.C.

Reexamination Requests:
No. 90/004,457, Nov. 12, 1996
No. 90/004,724, Aug. 14, 1997

Reexamination Certificate for:
Patent No.: 4,949,718
Issued: Aug. 21, 1990
Appl. No.: 242,730
Filed: Sep. 9, 1988

[51] Int. Cl.$^6$ .................................................. A61F 7/12
[52] U.S. Cl. ........................................................ 606/27
[58] Field of Search ............................. 600/18; 604/99; 606/27, 28

[56] References Cited

U.S. PATENT DOCUMENTS

| | | |
|---|---|---|
| 1,786,373 | 12/1930 | Walker . |
| 3,417,746 | 12/1968 | Moore et al. ........................... 128/8 |
| 4,160,455 | 7/1979 | Law ........................................ 128/400 |
| 4,676,258 | 6/1987 | Inokuchi et al. ....................... 128/804 |
| 4,754,752 | 7/1988 | Ginsburg et al. ................. 128/303.12 |
| 4,793,351 | 12/1988 | Landman et al. ...................... 128/344 |
| 4,799,479 | 1/1989 | Spears ................................. 128/303.1 |

FOREIGN PATENT DOCUMENTS

| | | |
|---|---|---|
| 895046 | 11/1952 | Germany . |
| 63-43661 | 2/1988 | Japan . |

OTHER PUBLICATIONS

F. H. Bardenheuer, "On a New Simple Method for Stopping Serious Uterus Bleeding", *Müchener Medizinishche Wochenscrift*, pp. 1546–1547 (18 Sep. 1936). [Translation attached.]

F. H. Bardenheuer, "Electrocoagulation of the Uterus Mucosa for the Treatment of Climacterical Bleeding", *Bardenheuer, Elektrokagulation der Uterusschleimbaut*, pp. 209–210 (1936). [Translatoin attached.]

A. Brothers, "Experiences with Intrauterine Vaporization", *The American Journal of Obstetrics and Diseases of Women and Children*, vol. XL, pp. 498–503, (Jul.–Dec. 1899).

H. Kraatz, "Concerning our Experiences with Atmokausis Uteri", *Zentralbatt Für Gynäkologie*, pp. 1329–1330 (6 Jun. 1936). [Translation attached.]

B.S. ten Berge, "The Treatment of Menstrual Disorders with Diathermia of the Uterus Mucosa—Report on Five Years Experience", *Zentralblatt for Gynakologie*, (1936), Nr. 5. [Translation attached.]

J. Markus, *Electronics Dictionary*, pp. 650–651 (1978).

A. R. Simpson, "Vaporisation (Atmokausis) of the Endometrium", *Scotish Med. and Surg. Journal*, pp. 499–505, (Jun. 1900).

F. K. Storm et al., "Hyperthermic Therapy for Human Neoplasms: Thermal Death Time", *Cancer*, vol. 46, pp. 1849–1854 (1980).

*Primary Examiner*—Max Hindenburg

[57] ABSTRACT

A method and apparatus for effecting necrosis of a tissue lining of a mammalian body cavity, particularly a uterine endometrium, by introducing an applicator comprising a distenable bladder connected to a catheter into the uterus, distending the bladder by introducing a non-toxic fluid under pressure, heating the fluid by means located internal to the bladder to a temperature of 190° to 215° F. and preferably 210° F. for a period of 4 to 12 minutes and preferably 6 minutes and regulating said apparatus by means located external to the uterus, thereby cauterizing substantially the entirety of the tissue lining, particularly the endometrium.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 19 are determined to be patentable as amended.

Claims 2–18 and 20, dependent on an amended claim, are determined to be patentable.

1. An apparatus for effecting necrosis of [an] *human* uterine endometrium comprising:
   a catheter [having a] *for insertion into human uterus via the cervical canal thereof, said catheter terminating in a rigid, axially closed* proximal end *portion* and [a] *having an open* distal end;
   a distendable bladder [means] *defining an enclosure* attached to said proximal end *portion* for insertion into and distending the uterus, *and for contacting substantially all of said endometrium; said distendable bladder projecting axially beyond the proximal end of the catheter when distended*;
   inflating means connected to said distal end for introducing an inflation medium into said bladder;
   heating means for heating said inflation medium to a temperature sufficient to effect tissue necrosis positioned internal to said bladder; and
   control means connected to said distal end for regulating the inflating and heating of said bladder.

19. An apparatus for effecting necrosis of [a tissue lining in a body cavity] *human uterine endometrium* comprising:
   a catheter *for insertion into human uterus and* comprising a length of flexible tubing having [a] *an open* distal end and [a] *an axially closed, rigid* proximal end *portion*;
   a bladder means for insertion into and distending the [body cavity] *uterus and* attached to [a] *the* proximal end *portion, said bladder means extending beyond the proximal end of the catheter when distended*;
   inflating means connected to said distal end for introducing an inflation medium through said flexible tubing and into said bladder;
   a heating means for heating said inflation medium to a temperature sufficient to effect tissue necrosis positioned internal to said bladder; and
   control means connected to said distal end for regulating inflation and heating of said bladder.

* * * * *